US007962899B2

(12) United States Patent
Thompson et al.

(10) Patent No.: US 7,962,899 B2
(45) Date of Patent: Jun. 14, 2011

(54) SYSTEM FOR MONITORING A TARGET APPLICATION AND METHOD THEREOF

(75) Inventors: David Scott Thompson, Tempe, AZ (US); Marc Alan Lottman, Mesa, AZ (US); Gary Owen McCullough, Charlottesville, VA (US); Jeffrey R Swenson, Layton, UT (US); Jun Ping Zhang, Scottsdale, AZ (US); Darrell Gene Hansen, Layton, UT (US)

(73) Assignee: Harris Corporation, Melbourne, FL (US)

( * ) Notice: Subject to any disclaimer, the term of this patent is extended or adjusted under 35 U.S.C. 154(b) by 1061 days.

(21) Appl. No.: 11/608,000

(22) Filed: Dec. 1, 2006

(65) Prior Publication Data

US 2008/0134147 A1 Jun. 5, 2008

(51) Int. Cl.
*G06F 9/44* (2006.01)
(52) U.S. Cl. ............. 717/127; 717/106; 717/168; 705/2
(58) Field of Classification Search .................. 717/106, 717/124–139, 168; 705/2
See application file for complete search history.

(56) References Cited

U.S. PATENT DOCUMENTS

| 4,646,226 A * | 2/1987 | Moon .............................. 700/71 |
| 4,764,763 A | 8/1988 | Wickstead et al. |
| 4,841,291 A | 6/1989 | Swix et al. |
| 5,261,820 A | 11/1993 | Slye et al. |
| 5,701,139 A | 12/1997 | Weinbaum et al. |
| 5,734,871 A | 3/1998 | Kleinerman et al. |
| 6,046,741 A | 4/2000 | Hochmuth |
| 6,243,707 B1 | 6/2001 | Humpleman et al. |
| 6,452,606 B1 | 9/2002 | Luzzatto |
| 6,466,240 B1 | 10/2002 | Maslov |
| 6,518,978 B1 | 2/2003 | Omaha et al. |
| 6,532,023 B1 | 3/2003 | Schumacher et al. |
| 6,674,447 B1 | 1/2004 | Chiang et al. |
| 6,681,387 B1 * | 1/2004 | Hwu et al. ..................... 717/158 |
| 6,690,392 B1 | 2/2004 | Wugoski |
| 6,757,905 B1 * | 6/2004 | Friedman et al. ............. 719/320 |

(Continued)

FOREIGN PATENT DOCUMENTS

| WO | 01/16720 | 3/2001 |
| WO | 02/48865 | 6/2002 |

OTHER PUBLICATIONS

Newberger et al., Designer support for context monitoring and control, Citeseer, 2003, pp. 1-11.*

(Continued)

*Primary Examiner* — Wei Y Zhen
*Assistant Examiner* — Satish Rampuria
(74) *Attorney, Agent, or Firm* — Bryan Cave LLP

(57) ABSTRACT

A system (100) for monitoring one ore more target application (192, 193) includes an application extender module (111) having a foreign communications module (114) to communicate a change in a first context in the one or more target applications to one or more foreign applications (190). The system also includes one or more first monitor modules (120, 130) having: (a) one or more capture modules (121, 131) to capture an event in the target applications; (b) one or more comparison modules (122, 132) to test whether the event includes the change in the first context; and (c) one or more first communications modules (123, 133) to communicate the change in the first context out of the target applications to the application extender module.

36 Claims, 7 Drawing Sheets

U.S. PATENT DOCUMENTS

| | | | |
|---|---|---|---|
| 6,842,755 | B2 | 1/2005 | Maslov |
| 6,864,901 | B2 | 3/2005 | Chang et al. |
| 6,933,556 | B2 | 8/2005 | Endoh et al. |
| 6,941,313 | B2 | 9/2005 | Seliger et al. |
| 6,971,067 | B1 | 11/2005 | Karson et al. |
| 7,526,488 | B2 * | 4/2009 | Herold ................................ 1/1 |
| 2005/0137908 | A1 * | 6/2005 | Fusari et al. ...................... 705/2 |
| 2005/0160371 | A1 | 7/2005 | Karson et al. |
| 2005/0165790 | A1 | 7/2005 | Seliger et al. |
| 2006/0075020 | A1 | 4/2006 | Seliger et al. |
| 2006/0080141 | A1 | 4/2006 | Fusari |

OTHER PUBLICATIONS

U.S. Appl. No. 09/583,301, filed May 30, 2000, Seliger, et al.

Three Ways to Inject Your Code Into Another Process; http://www.codeproject.com/threads/winpsy.asp; retrieved from the internet on Nov. 17, 2006; 19 pages.

Understanding the Import Address Table; http://sandsprite.com/CodeStuff/Understanding_imports.html; retrieved from the internet on Aug. 31, 2006; 8 pages.

HL7 Australia CCOW Resources Page; http://www.hl7.org.au/CCOW.htm; retrieved from the internet on Jun. 28, 2006; 2 pages.

Fusion from Carefx™; The First Patient Information Aggregation platform for the healthcare industry; 10 pages.

HL7 Context Management "CCOW" Standard: Component Technology Mapping: Web/HTTP, Draft Version 1.5, Jan. 19, 2003; 72 pages.

HL7 Context Management "CCOW" Standard: Component Technology Mapping: ActiveX, Draft Version 1.5, Apr. 30, 2003; 49 pages.

HL7 Context Management "CCOW" Draft Standard: Subject Data Definitions, Version 1.5, Apr. 30, 2003; 58 pages.

HL7 Context Management "CCOW" Standard: Technology- and Subject-Independent Component Architecure, Draft Version 1.5, Apr. 30, 2003; 225 pages.

Web Services Coordination (WS-Coordination); Version 1.0; Aug. 2005; 23 pages.

HL7 Context Management "CCOW" Standard: Component Technology Mapping: ActiveX,; Version 1.5; May 2004; 50 pages.

HL7Context Management "CCOW" Standard: Technology—and Subject—Independent Component Architecture; Version 1.5; May 2004; 223 pages.

HL7 Context Management "CCOW" Standard: Subject Data Definitions; Version 1.5; May 2004; 47 pages.

HL7 Context Management "CCOW" Standard: Component Technology Mapping: Web/HTTP; Version 1.5; May 2004; 74 pages.

HL7 Context Management "CCOW" Standard: User Interface: Microsoft Windows and Web; Version 1.5; May 2004; 16 pages.

PCT International Publication No. WO 01/11464 for International Application No. PCT/US00/14942.

PCT International Publication No. WO 00/59286 for International Application No. PCT/US00/09348.

* cited by examiner

SYSTEM FOR MONITORING A TARGET APPLICATION AND METHOD THEREOF

FIELD OF THE INVENTION

This invention relates to a computer monitoring system, in general, and relates to a computer system for monitoring changes in one or more variables in one or more target applications, in particular.

BACKGROUND OF THE INVENTION

When using a computer, a user may change a variable or an item in a first computer application and may want this change to be transferred, duplicated, or copied by other active computer applications. In this manner, the other active computer applications are synchronized with the first computer application. For example, a person might login to a database or a network using a first application on a computer and might want other computer programs to login to the same database or network using the same login information entered into the first computer application. In another example, in the field of medicine, a nurse or a doctor can load data regarding one patient into one computer application and might want other computer applications also to load data regarding the same patient.

When synchronizing computer applications, the first step in the process is detecting a change in a variable or an item in a target application. If the target application is not designed to be synchronized with other programs, however, monitoring and automatically detecting changes of variables in the target application can be difficult.

One traditional technique used to monitor and detect changes in a target application involves screen scraping. Screen scraping can entail using a monitoring program separate from the target application to capture an image of a window of the target application or the whole computer screen. The monitoring program compares the captured image to previously collected images to determine if any changes in the application have occurred. Without an event or some external stimuli to trigger the occurrence of a screen scrape, traditional monitoring programs check for changes by performing screen scrapes at regular time intervals, which is a process known as polling.

Using screen scraping to detect changes in the target application has several disadvantages. For example, screen scraping requires the transfer of large amounts of data on the computer system bus or the network, and this data transfer can dramatically slow down the computer and/or the network. In addition, polling can miss variable changes. For example, if the target application is polled once a second and the variable changes twice during a second, the monitoring application will miss the first change. Furthermore, if the variable changes occur at large time intervals compared to the polling interval, computer resources are needlessly wasted by checking continuously for variable changes. For example, if a variable change occurs only once every few minutes and if the monitoring program polls the target application every half second, computer processor time and system resources are wasted.

Thus, a need exists for a computer system to monitor target applications that more efficiently uses computer resources.

BRIEF DESCRIPTION OF THE DRAWINGS

The invention will be better understood from a reading of the following detailed description, taken in conjunction with the accompanying figures in the drawings in which.

Figure 1:
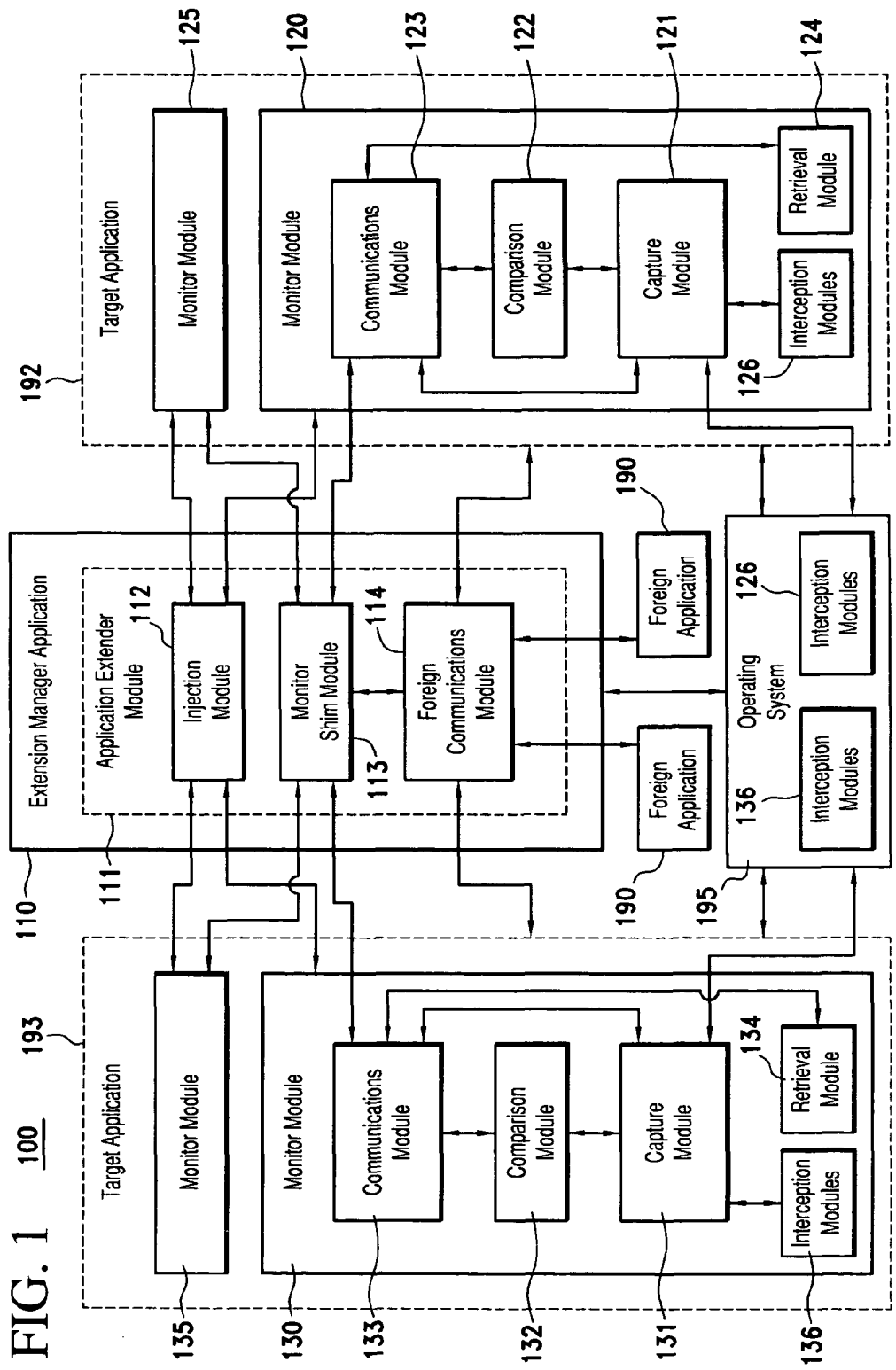
FIG. 1 illustrates a block diagram of a system for monitoring target applications, according to a first embodiment.

For simplicity and clarity of illustration, the drawing figures illustrate the general manner of construction, and descriptions and details of well-known features and techniques may be omitted to avoid unnecessarily obscuring the invention. Additionally, elements in the drawing figures are not necessarily drawn to scale. For example, the dimensions of some of the elements in the figures may be exaggerated relative to other elements to help improve understanding of embodiments of the present invention. The same reference numerals in different figures denote the same elements.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments of the invention described herein are, for example, capable of operation in sequences other than those illustrated or otherwise described herein. Furthermore, the terms "include," "have," and any variations thereof, are intended to cover a non-exclusive list, such that a process, method, article, or apparatus that comprises a list of elements is not necessarily limited to only those elements, but may include other elements not expressly listed or inherent to such process, method, article, or apparatus.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments of the invention described herein are, for example, capable of operation in other orientations than those illustrated or otherwise described herein. The term "coupled," as used herein, is defined as directly or indirectly coupled in an electrical or non-electrical manner.

DETAILED DESCRIPTION OF THE DRAWINGS

In an embodiment, a system for monitoring a target application includes: (a) an application extender module having a foreign communications module to communicate a change in a first context in the target application to one or more foreign applications; and (b) a first monitor module including: (1) a capture module to capture an event in the target application; (2) a comparison module to test whether the event includes the change in the first context; and (3) a first communications module to communicate the change in the first context out of the target application to the application extender module.

In a further embodiment, a method of monitoring one or more target applications includes:

(a) capturing a first event in a first target application of the one or more target applications;

(b) testing in the first target application whether the first event includes a change in a first context;

(c) if the first event includes the change in the first context, transmitting first data indicating the change in the first context from the first target application to an extension manager application; and (d) afterwards, transmitting the change in the first context from the extension manager application to one or more foreign applications.

Turning to the figures, FIG. 1 is a block diagram of a system 100 for monitoring one or more of target applications 192 and 193. In a different embodiment, system 100 has only one target application or has more than two target applications. System 100 can also be considered a system capable of controlling one or more foreign applications 190. In one embodiment, system 100 can control foreign applications 190 by communicating context changes in target applications 192 and/or 193 to foreign applications 190. In some embodiments, system 100 can monitor target applications 192 and 193 and control the behavior of foreign applications 190 without modifying the source or binary code for target applications 192 and 193 and foreign applications 190. It should be understood that system 100 is merely exemplary and that the present invention may be employed in many embodiments not specifically depicted or otherwise described herein.

As an example, system 100 can include: (a) an extension manager application 110 capable of receiving at least one change in one or more contexts in target application 192 or 193 and also capable of communicating the context change(s) to one or more foreign applications 190; and (b) a monitor module 120 capable of detecting the at least one change in the contexts in target application 192. System 100 also can include a monitor module 130 capable of detecting changes in one or more context(s) in target application 193. Application 110 is separate from target applications 192 and 193. Monitor modules 120 and 130 are part of target applications 192 and 193, respectively, and can be similar to each other. In some embodiments, monitor modules 120 and 130 are not natively part of target applications 192 and 193, respectively. Rather, monitor modules 120 and 130 are injected into target applications 192 and 193, respectively, and run in the same shared memory space.

In one embodiment, application 110 can include an application extender module 111. Application extender module 111 can comprise: (a) a foreign communications module 114 to communicate the context changes in target applications 192 and/or 193 to one or more of foreign applications 190; (b) an injection module 112 to inject monitor modules 120 and 130 into target applications 192 and 193, respectively; and (c) a monitor shim module 113 to communicate to monitor modules 120 and 130 the context(s) to be monitored. In some embodiments, monitor shim module 113 also handles other communications with monitor modules 120 and 130. In other embodiments, other modules handle the other communications with monitor modules 120 and 130.

In the same or a different embodiment, monitor module 120 includes: (a) a capture module 121 to capture an event in target application 192; (b) a comparison module 122 to test whether the event includes any change in the context(s); and (c) communications module 123 to communicate the change in the contexts out of target application 192 and to monitor shim module 113. Similarly, monitor module 130 can include a capture module 131, a comparison module 132, and a communications module 133, which can be identical or substantially similar to capture module 121, comparison module 122, and communications module 123, respectively.

In one embodiment, monitor modules 120 and 130 further include optional retrieval modules 124 and 134, respectively, to obtain the context from target applications 192 and 193 after comparison modules 122 and 132 have detected the change in the first context(s). In a different embodiment, capture modules 121 and 131 can perform this same function.

In some embodiments, system 100 further includes monitor modules 125 and 135. In one example, monitor modules 125 and 135 can be identical to or substantially similar to monitor modules 120 and 130, respectively.

"System," as used herein, can refer to, or otherwise include, one computer application or two or more computer applications. "Target application" as used herein, can refer to, or otherwise include, a single computer application or two or more computer applications, other than application 110 or an operating system 195. "Foreign applications," as used herein, can refer to, or otherwise include, one or more computer applications, other than application 110, or operating system 195. Foreign applications 190 can communicate with application 110 directly or indirectly through other applications, a network, and/or operating system 195. In some embodiments, one application can function as both a target application and a foreign application. For example, system 100 can monitor a first application for context changes while communicating any context changes from one or more second applications to this first application.

Operating system 195 is a software program that manages the hardware and software resources of a computer and/or a computer network. Operating system 195 performs basic tasks such as, for example, controlling and allocating memory, prioritizing the processing of instructions, controlling input and output devices, facilitating networking, and managing files. Examples of common operating systems include Microsoft® Windows, Mac® OS, UNIX® OS, and Linux® OS. Application 110, foreign applications 190, target applications 192 and 193, and operating system 195 can be located on the same computer and/or on different computers on the same computer network.

"Context," as used herein, refers to or otherwise includes an identifying variable or variables in the target application that can be changed, manipulated, defined, or set by a user or foreign applications. For example in the health care field, when viewing patient information, the context can be the patient identifier ("ID") in the database or on the network. When logging into a network, the context can be the user ID. In another example, when entering billing information into an accounting application, the context can be the transaction number and/or the customer number.

"Event," as used herein, refers to or otherwise includes the occurrence or non-occurrence of an item, incident, or action in the target applications, the operating system, or another application other than foreign applications 190 and application 110. Examples of events include, but are not limited to: (1) the creation, modification, activation, or destruction of a window or a menu; (2) the gain or loss of focus of a window; (3) the selection of a menu; (4) the pressing of a button in a window or on a computer keyboard; (5) a state change of a window, a menu, or a button; (6) a selection from a list box, a tool box, or a combo box; (7) a change in an edit box; (8) a mouse click; (9) a title bar change; or (10) a text label change.

Interception modules 126 and 136 in FIG. 1 are explained hereinafter.

Figure 2:
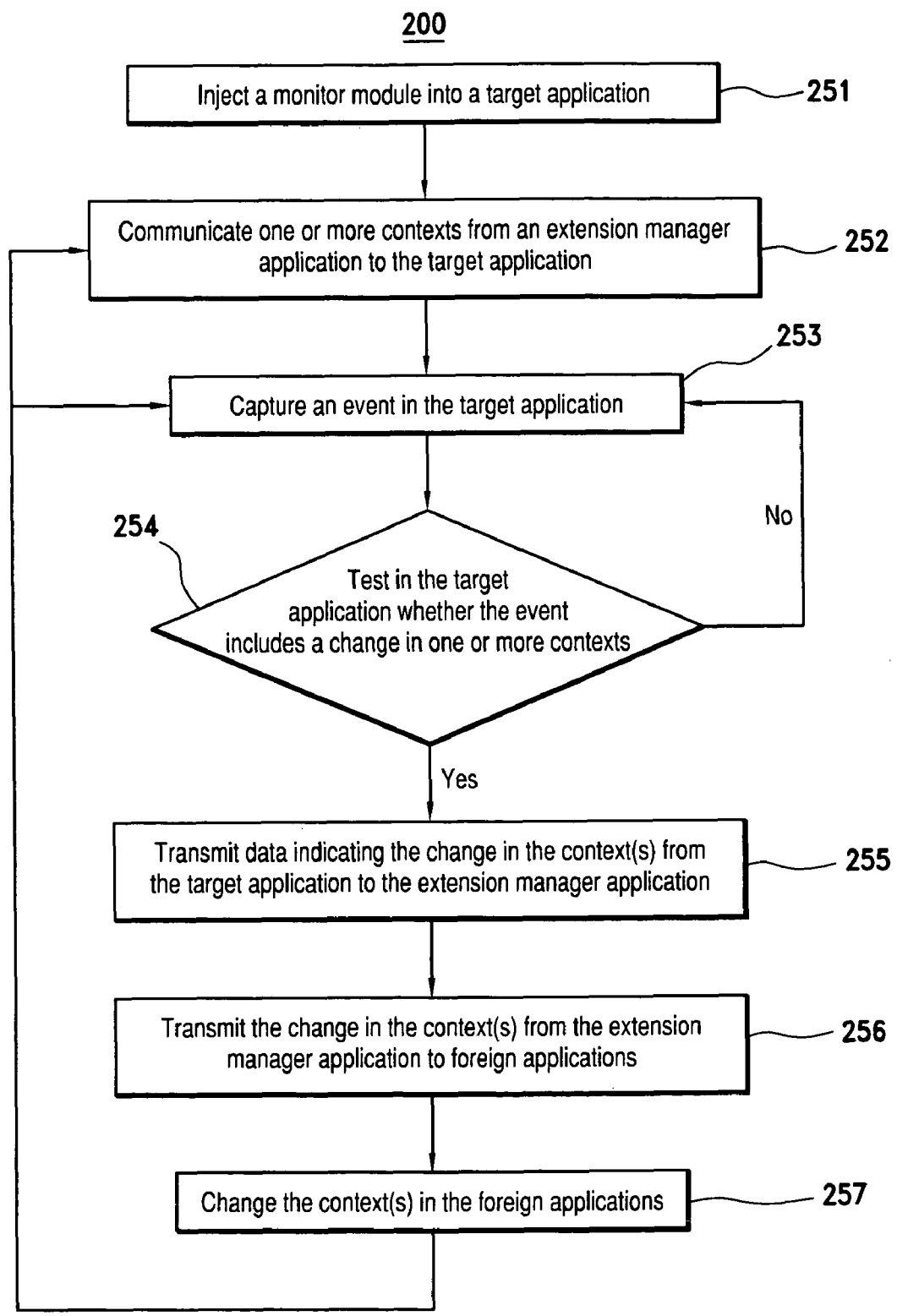
FIG. 2 illustrates a flow chart for a method of monitoring the target applications using the system of FIG. 1, according to the first embodiment.

FIG. 2 illustrates a flow chart for a method 200 of monitoring target applications 192 and 193 (FIG. 1) using system 100 (FIG. 1), according to the first embodiment. It should be appreciated that this method is merely illustrative of a technique for implementing the various aspects of one embodiment described herein and that system 100 (FIG. 1) and method 200 are not limited to this particular embodiment, as numerous other embodiments are possible. For example, the techniques illustrated in FIG. 2 can be implemented using the Microsoft® Windows platform or by using Java® platform.

In one embodiment, a first step 251 of monitoring target application 192 (FIG. 1) is injecting monitor module 120 (FIG. 1) into target application 192 (FIG. 1). In one embodiment, injection module 112 (FIG. 3) injects monitor module 120 (FIG. 1). In one example, monitor module 120 (FIG. 1) can be included in a DLL (dynamically linked library). A DLL is an executable file that acts as a shared library of functions. In one embodiment, a DLL (not shown) containing monitor module 120 (FIG. 1) can be mapped into the address space of target application 192 (FIG. 1). For example, in some versions of Microsoft Windows, the DLL can be mapped into the address space of target application 192 (FIG. 1) using the SetWindowHookEx API (application program interface). The SetWindowHookEx API is a standard API used with some versions of Microsoft Windows. In other embodiments, functions designed to work with target application 192 (FIG. 1) can be used to inject monitor module 120 (FIG. 1).

The method used to inject monitor module 120 (FIG. 1) depends on the specifics of operating system 195 (FIG. 1) and target application 192 (FIG. 1). That is, if operating system 195 (FIG. 1) is a version of Microsoft Windows, the aforementioned injection method involving the Microsoft Windows API can be used. However, if operating system 195 (FIG. 1) is a version of Mac OS, UNIX, or Linux, for example, different injection methods can be used.

In the same or a different embodiment of step 251, monitor module 130 (FIG. 1) can be injected into target application 193 (FIG. 1) using an identical or substantially similar method as used to inject monitor module 120 (FIG. 1). In another embodiment, a first injection method is used to inject monitor module 120 (FIG. 1), and a second injection method different from the first method is used to inject monitor modules 125, 130 and/or 135 (FIG. 1). One or more injection modules can inject monitor modules 120, 125, 130 and/or 135 simultaneously or sequentially.

After step 251, a step 252 of method 200 involves communicating one or more contexts from application 110 (FIG. 1) to target application 192 (FIG. 1). The contexts communicated in this step can be the contexts that will be monitored by monitor module 120 (FIG. 1).

In one embodiment, monitor shim module 113 (FIG. 1) communicates the contexts to communications module 123 (FIG. 1) after monitor module 120 (FIG. 1) is injected into target application 192 (FIG. 1). Communications module 123 (FIG. 1) then communicates the contexts to capture module 121 (FIG. 1) and comparison module 122 (FIG. 1). In other embodiments, the contexts are imbedded into monitor module 120 (FIG. 1) before monitor module 120 (FIG. 1) is injected into target application 192 (FIG. 1). That is, in this embodiment, step 252 occurs simultaneously with step 251.

In the example where operating system 195 (FIG. 1) is a version of Microsoft Windows, the contexts can be communicated from application 110 (FIG. 1) to monitor module 120 (FIG. 1) using the standard Microsoft Windows system APIs. In other embodiments, application 110 does not directly communicate the contexts to monitor module 120 (FIG. 1). In one example, application 110 can write the contexts to the memory of the computer (e.g., a location in the shared memory of the computer). Then, application 110 (FIG. 1) can send a message to monitor module 120 (FIG. 1) notifying monitor module 120 (FIG. 1) that the contexts are stored in memory, and communications module 123 can retrieve the contexts from memory. In some embodiments, the message includes the address in the memory where the contexts are stored.

In the same or a different embodiment of step 252, one or more contexts can be communicated to monitor module 130 (FIG. 1) by application 110 (FIG. 1) using a method identical to or substantially similar to the method used to communicate the contexts to monitor module 120 (FIG. 1). One or more monitor shim modules can communicate the one or more contexts to monitor modules 120, 125, 130, and 135 sequentially or simultaneously with each other.

In one embodiment, monitor shim module 113 (FIG. 1) can communicate one or more first contexts to communications module 123 (FIG. 1) and one or more second contexts different from the first contexts to communications module 133 (FIG. 1). In a further embodiment, monitor shim (FIG. 1) can communicate the same one or more contexts to communications modules 123 and 133 (FIG. 1). In some embodiments, monitor shim module 113 (FIG. 1) also communicates to monitor modules 120 and 130 (FIG. 1) the current values for the contexts.

In a non-illustrated embodiment, application extender module 111 (FIG. 1) includes two monitor shim modules. In this embodiment, one monitor shim module communicates the contexts to monitor module 120 (FIG. 1), and the second monitor shim module communicates the contexts to monitor module 130 (FIG. 1).

In yet another embodiment, monitor shim module 113 (FIG. 1) communicates one or more first contexts to monitor module 120 (FIG. 1) and one or more second contexts, different from the first contexts, to monitor module 125 (FIG. 1). Similarly, monitor shim module 113 (FIG. 1) can communicate one or more third contexts to monitor module 130 (FIG. 1) and one or more fourth contexts, different from the third contexts, to monitor module 135 (FIG. 1).

Figure 3:
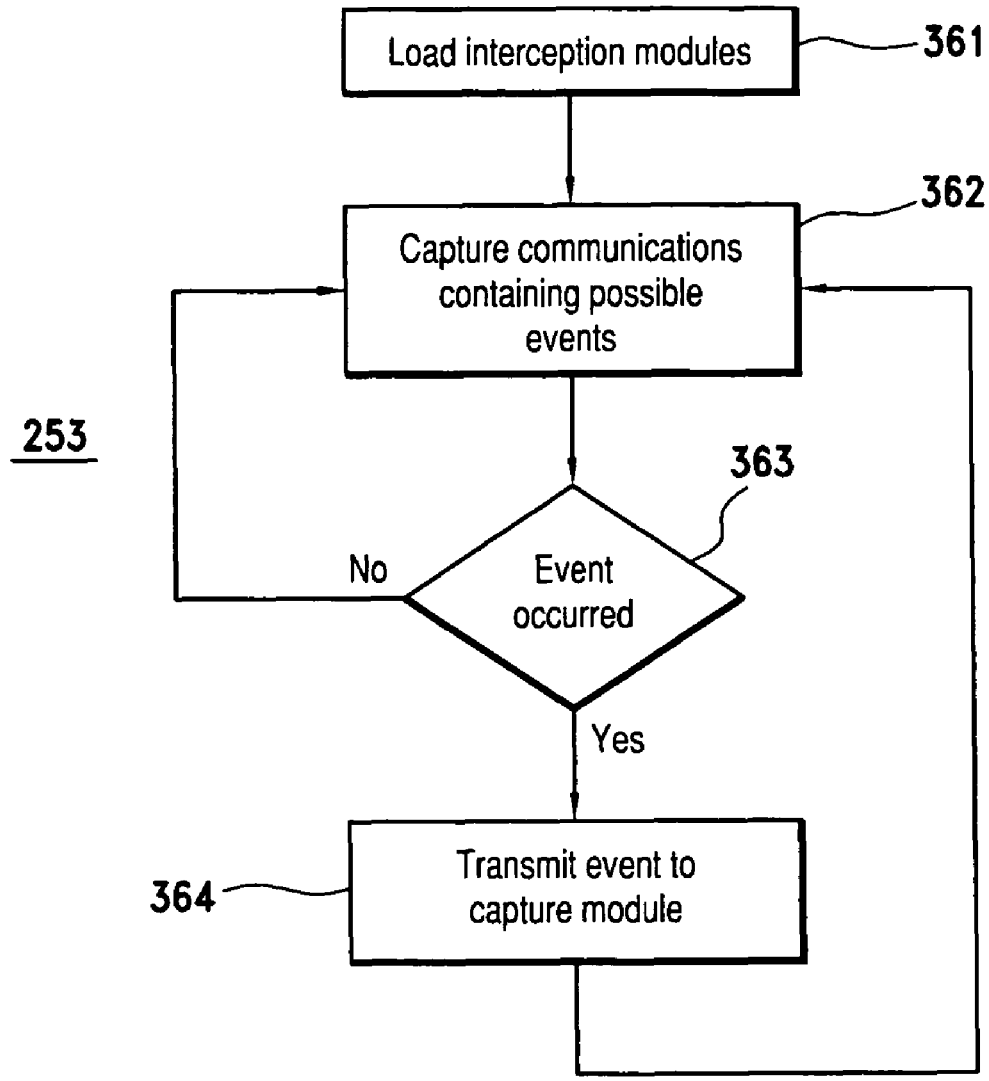
FIG. 3 illustrates a flow chart describing a process of capturing an event in the target application, according to the first embodiment.

Following the communicating of the contexts to monitor module 120 (FIG. 1), a step 253 in method 200 is capturing an event in target application 192 (FIG. 1). FIG. 3 illustrates a flow chart describing step 253 of capturing an event in target application 192 (FIG. 1), according to an embodiment.

Referring to FIG. 3, a first process 361 of step 253 is loading one or more interception modules 126 (FIG. 1) in target application 192 (FIG. 1) and/or operating system 195 (FIG. 1). In one example, capture module 121 (FIG. 1) loads interception modules 126 (FIG. 1).

In some embodiments, interception modules 126 (FIG. 1) are loaded into operating system 195 (FIG. 1) but not loaded in target application 192 (FIG. 1). In another embodiment, interception modules 126 (FIG. 1) are loaded in target application 192 (FIG. 1), but not loaded in operating system 195 (FIG. 1). In a further embodiment, interception modules 126 (FIG. 1) are loaded in operating system 195 (FIG. 1) and target application 192 (FIG. 1). In a non-illustrated embodiment, interception modules 126 (FIG. 1) are loaded into target application 192 (FIG. 1) before or simultaneously with the one or more contexts being communicated to target application 192 (FIG. 1).

In one embodiment, interception modules 126 (FIG. 1) are hooks. In this embodiment, capture module 121 (FIG. 1) uses hooks to intercept the event. Hooks are pointers in the operating system's message-handling mechanism where an application can load a subroutine to monitor the message traffic in operating system 195 (FIG. 1) and process certain types of messages before they reach target application 192 (FIG. 1).

Hooks, as used herein, can refer to any method, pointer, or variable used to access message traffic in any operating system and is not limited to the example of Microsoft Windows described below.

In the example where operating system 195 (FIG. 1) is a version of Microsoft Windows, interception modules 126 (FIG. 1) can use standard Microsoft Windows hooks, which are specified in the Microsoft Window API (e.g., WH_CALLWNDPROC, WH_CALLWNDPROCRET, WH_CBT, WH_FOREGROUNDIDLE, WH_GETMESSAGE, WH_JOURNALPLAYBACK, WH_JOURNALRECORD, WH_KEYBOARD, and WH_MOUSE hooks). In the same or a different embodiment, interception modules 126 (FIG. 1) can include one or more hooks designed to be used with target application 192.

In another embodiment, interception modules 126 (FIG. 1) can be modules used to intercept calls to functions within target application 192 (FIG. 1). In the example where operating system 195 (FIG. 1) is a version of Microsoft Windows, interception modules 126 (FIG. 1) can redirect function calls by modifying the Import Address Table (IAT) (not shown) in target application 192 (FIG. 1). The IAT is a pointer lookup table in target application 192 (FIG. 1) used when calling a Microsoft Windows API function. When calling a Microsoft Windows API function, applications will look up the memory address of the function in the IAT. In this method of intercepting events, the address in the IAT of one or more functions called by target application 192 (FIG. 1) are changed to a memory address containing interception modules 126 (FIG. 1). In one embodiment, the function calls redirected are function calls related to events. For example, interception modules 126 (FIG. 1) can intercept all function calls related to the creation, destruction, or modification of windows in target application 192 (FIG. 1).

In the same or a different embodiment, monitor module 130 (FIG. 1) can load interception modules 136 (FIG. 1) in target application 193 (FIG. 1) and/or operating system 195 (FIG. 1). In one example, interception modules 136 (FIG. 1) and the loading process of interception modules 136 (FIG. 1) are identical to or substantially similar to interception modules 126 (FIG. 1) and the process of loading interception modules 126 (FIG. 1), respectively.

Next, a process 362 of step 253 is capturing communications containing possible events. In one embodiment, interception modules 126 (FIG. 1) can be used to intercept events while the events are being communicated between target application 192 (FIG. 1) and operating system 195 (FIG. 1). In one example, interception modules 126 (FIG. 1) are application (i.e., thread) specific hooks. That is, interception modules 126 (FIG. 1) only monitor communicates associated with target application 192 (FIG. 1).

In another embodiment, interception modules 126 (FIG. 1) can be global hooks. That is, interception modules 126 (FIG. 1) monitor every message sent between operating system 195 (FIG. 1) and any application running on operating system 195 (FIG. 1).

In a further embodiment, capture module 121 (FIG. 1) can intercept the events while the events are being communicated within target application 192 (FIG. 1). In one example, the events are intercepted while being communicated between functions in target application 192 (FIG. 1). For example, capture module 121 (FIG. 1) could have modified the IAT to redirect one or more function calls to interception modules 126 (FIG. 1). After examining the function calls for events, interception modules 126 (FIG. 1) can forward the functions to target application 192 (FIG. 1).

Figure 4:
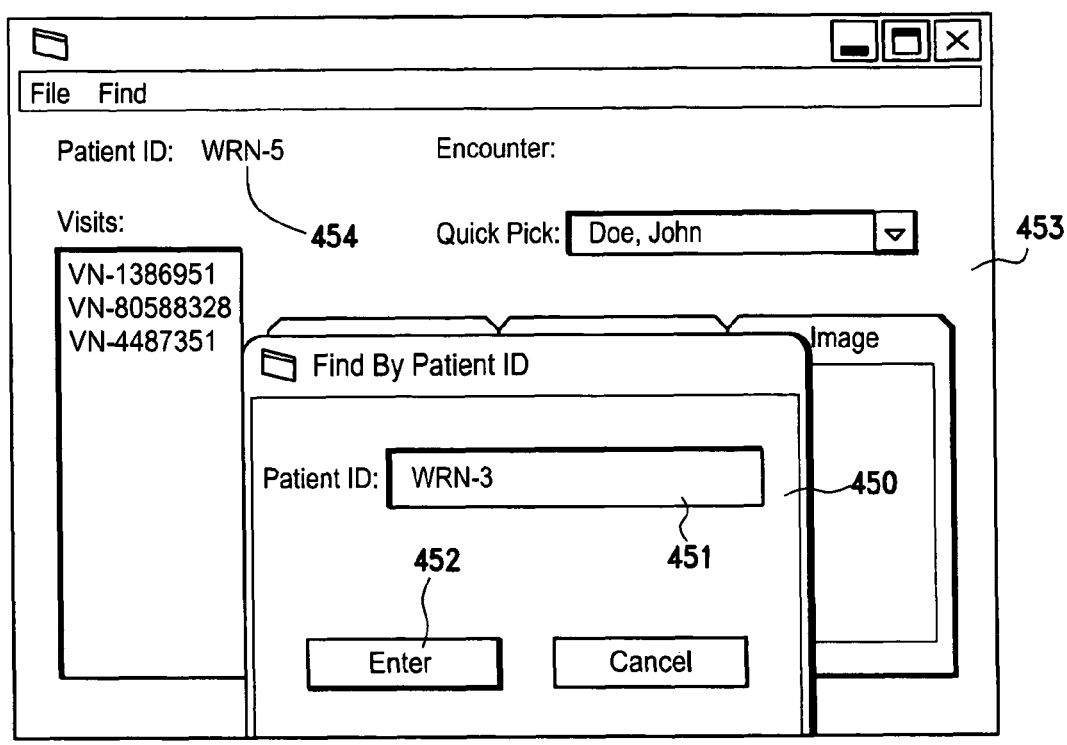
FIG. 4 illustrates a window created by a target application that allows a user to change a context, according to one embodiment.

A specific example of an event that can be captured is shown in FIG. 4. FIG. 4 illustrates windows 450 and 453 that are created by target application 192 (FIG. 1). Windows 450 and 453 allow a user to change a context, according to one embodiment. In this example, the user can enter a value for the patient ID (i.e., the context) into a text box 451. After typing the patient ID into text box 451, the user clicks on a button 452 to change the context. After clicking button 452, operating system 195 (FIG. 1) sends a message to target application 192 containing information about the change. In one embodiment, interception modules 126 (FIG. 1) can intercept this communication from operating system 195 (FIG. 1).

In another embodiment, capture module 121 (FIG. 1) can intercept communications regarding the change in patient ID while the information is being communicated within target application 192 (FIG. 1). For example, after target application 192 (FIG. 1) receives the information about the event from operating system 195 (FIG. 1), interception modules 126 can intercept a function call, which instructs window 453 to update text 454 in window 453 to "WRN-3".

Referring back to FIG. 1, in the same or a different embodiment, monitor module 130 can similarly capture communications containing possible events. Monitor module 130 can intercept information about the context while the information is communicated between operating system 195 and target application 193 or within target application 193. In one example, monitor module 130 uses interception modules 136 to intercept the event. Interception modules 136 can be identical to or substantially similar to interception modules 126.

Referring again to FIG. 3, after process 362, a process 363 of step 253 is checking the intercepted communications for an occurrence of an event. In one embodiment, after communications containing a possible event are captured in process 362, capture module 121 (FIG. 1) examines the intercepted communication to see if an event occurred.

In one embodiment, capture module 121 (FIG. 1) sorts through the intercepted communications looking for functions calls or other information related to an event. If an event has not occurred, the intercepted information is discarded and/or forwarded to target application 192 (FIG. 1) and process 362 is repeated.

In another embodiment, capture module 121 (FIG. 1) only intercepts function calls related to events, and process 363 of checking the intercepted communications for an occurrence of an event is unnecessary and redundant. In the same or a different embodiment, process 363 can be skipped, and a process 364, described below, is performed immediately following process 362.

Capture module 131 (FIG. 1) can check for an occurrence of an event in the communications intercepted by interception modules 136 (FIG. 1). Capture module 131 (FIG. 1) can use an identical or substantially similar method as used by capture module 121 (FIG. 1) to check the intercepted communications.

After an event is detected by capture module 121 (FIG. 1), process 364 of step 253 is transmitting the event to comparison module 122 (FIG. 1). In one embodiment, the information related to the event can be passed directly from capture module 121 (FIG. 1) to comparison module 122 (FIG. 1). In another embodiment, the information related to the event can be written to memory by capture module 121 (FIG. 1), and a message can be communicated from capture module 121 (FIG. 1) to comparison module 122 (FIG. 1) informing comparison module 122 (FIG. 1) that an event has occurred, and the event information is stored in memory. After sending the information, capture module 121 (FIG. 1) continues to monitor communications in process 362 until another possible event occurs or the monitoring process is terminated.

In the same or a different embodiment, after detecting an event, capture module 131 (FIG. 1) can use the identical or a substantially similar process as used by capture module 121 (FIG. 1) to communicate information about the event to comparison module 132 (FIG. 1).

Referring back to FIG. 2, the next step in method 200 is step 254 to test in target application 192 (FIG. 1) whether the event includes a change in one or more contexts. In one embodiment, comparison module 122 (FIG. 1) tests whether the event include any context changes. In one embodiment, comparison module 122 (FIG. 1) is programmed to recognize that changes in certain variables or modification to specific portions of windows related to target application 192 (FIG. 1) indicate a context has changed.

In one example, the event captured in step 253 could include an instruction from target application 192 (FIG. 1) to change some text displayed in a window. For instance, the event could include an instruction to change text 454 (FIG. 4) displayed in window 453 (FIG. 4). Comparison module 122 (FIG. 1) recognizes that this text change indicates that a first context has changed to the new value indicated in the text. In one embodiment, after detecting the context change, comparison module 122 (FIG. 1) compares the current value for the first context with the new value to confirm a context change has occurred.

In one embodiment, retrieval module 124 (FIG. 1) is used to obtain the current value for the context to be monitored. In other embodiments, monitor shim module 113 (FIG. 1) communicates the context value to monitor module 120 (FIG. 1) in step 252.

In one embodiment, after testing whether the event includes a first context change, monitor module 120 (FIG. 1) can test whether the event includes a change in a second context. In one example, comparison module 122 (FIG. 1) tests whether the first event includes a change in the second context. After testing for changes in the first and second contexts, comparison module 122 (FIG. 1) tests for changes in other contexts communicated to monitor module 120 (FIG. 1) in step 252.

In another embodiment, monitor module 120 (FIG. 1) tests whether the event included a change in one or more first contexts, and monitor module 125 (FIG. 1) tests whether the event included a change in one or more second contexts, where the second contexts are different from the first contexts. Monitor modules 130 and 135 (FIG. 1) can perform similar functions as described for monitor modules 120 and 125 (FIG. 1).

If a context change did not occur, step 253 is repeated. However, if a context change occurred, a step 255 in method 200 transmits data indicating the change in the context from target application 192 (FIG. 1) to application extender module 111 (FIG. 1). In one embodiment, if the context change occurred in target application 192 (FIG. 1), the data is transmitted from target application 192 (FIG. 1) by communications module 123 (FIG. 1) to monitor shim module 113 (FIG. 1). In some embodiments, data indicating the change of the contexts is transmitted from target application 192 (FIG. 1) to application 110 (FIG. 1) only if the event includes context changes.

In the example where operating system 195 (FIG. 1) is a version of Microsoft Windows, the data can be communicated using standard Microsoft Windows APIs. In other examples, communications module 123 (FIG. 1) does not directly communicate the data to monitor shim module 113 (FIG. 1). Instead, communications module 123 (FIG. 1) writes the data to memory, and sends a message to monitor shim module 113 (FIG. 1) notifying it that data is available in memory. In some embodiments, the message includes the address in memory where the contexts are stored. In other embodiments, the message notifies monitor shim module 113 (FIG. 1) that an event has occurred.

If more than one context change occurred in the event, communications module 123 (FIG. 1) can first transmit data indicating the change in the first context from target application 192 (FIG. 1) to application 110 (FIG. 1). In one embodiment, after transmitting data regarding the first context change, communications module 123 (FIG. 1) transmits second data indicating the change in the second context from target application 192 (FIG. 1) to application 110 (FIG. 1). Subsequently, communications module 123 (FIG. 1) can transmit data regarding any other context changes to application 110 (FIG. 1). In another embodiment, communications module 123 (FIG. 1) simultaneously communicates the data regarding all of the context changes to application 110 (FIG. 1).

In the same or a different embodiment, if the context change occurs in target application 193 (FIG. 1), the data regarding the context change can be transmitted to monitor shim module 113 (FIG. 1) by communications module 133 (FIG. 1) using the same or a substantially similar method used by communications module 123 (FIG. 1).

Next, a step 256 in method 200 transmits the change in the context from application 110 (FIG. 1) to one or more of foreign applications 190 (FIG. 1). In one embodiment, foreign communications module 114 (FIG. 1) is capable of communicating the change in the context in target application 192 (FIG. 1) to foreign applications 190 (FIG. 1). In some embodiments, application 110 (FIG. 1) includes multiple foreign communications modules to communicate the changes in the context to multiple foreign applications 190 (FIG. 1).

In one embodiment, foreign communications module 114 (FIG. 1) communicates with foreign applications 190 (FIG. 1) in accordance with a Clinical Context Object Working Group standard. In another example, foreign communications module 114 (FIG. 1) communicates with foreign applications 190 (FIG. 1) using Transmission Control Protocol (TCP) and Internet Protocol (IP), i.e., TCP/IP.

In some embodiments, if the change in the context occurs in target application 192 (FIG. 1), the change in context is also communicated to target application 193 (FIG. 1). That is, target application 193 (FIG. 1) can function as a foreign application when the change in context occurs in target application 192 (FIG. 1). In one example, foreign communications module 114 communicates the change in context to target application 193 (FIG. 1). In another example, monitor shim module 113 can communicate the context change to target application 193 (FIG. 1). Similarly, when the context change occurs in target application 193 (FIG. 1), the change in context can be communicated to target application 192 (FIG. 1) by foreign communications module 114 (FIG. 1) or monitor shim module 113 (FIG. 1) in some embodiments.

After transmitting the change in the contexts from application 110 (FIG. 1) to foreign applications 190 (FIG. 1), a step 257 of method 200 changes the contexts in foreign applications 190 (FIG. 1). The method used to change a context in foreign applications 190 (FIG. 1) depends on the design and configuration of the specific foreign application. Some of foreign applications 190 (FIG. 1) are designed to receive the change in context and automatically change their context. In other examples, a first foreign application of foreign applications 190 can receive the change in context for a second foreign application of foreign applications 190 and then perform a script or program to change the context in the second foreign application.

In one embodiment, after changing the context in foreign applications 190 (FIG. 1), system 100 (FIG. 1) can continue to repeat steps 253 through step 257 until the monitor process is terminated. Steps 253 through step 257 can monitor a single change in a single context, or the process described in FIG. 2 can monitor simultaneously for multiple changes in multiple contexts. In another embodiment, after step 257, application extender module 111 (FIG. 1) can communicate one or more new contexts to target application 192 (FIG. 1) in step 253, and system 100 (FIG. 1) can monitor these new contexts.

Figure 5:
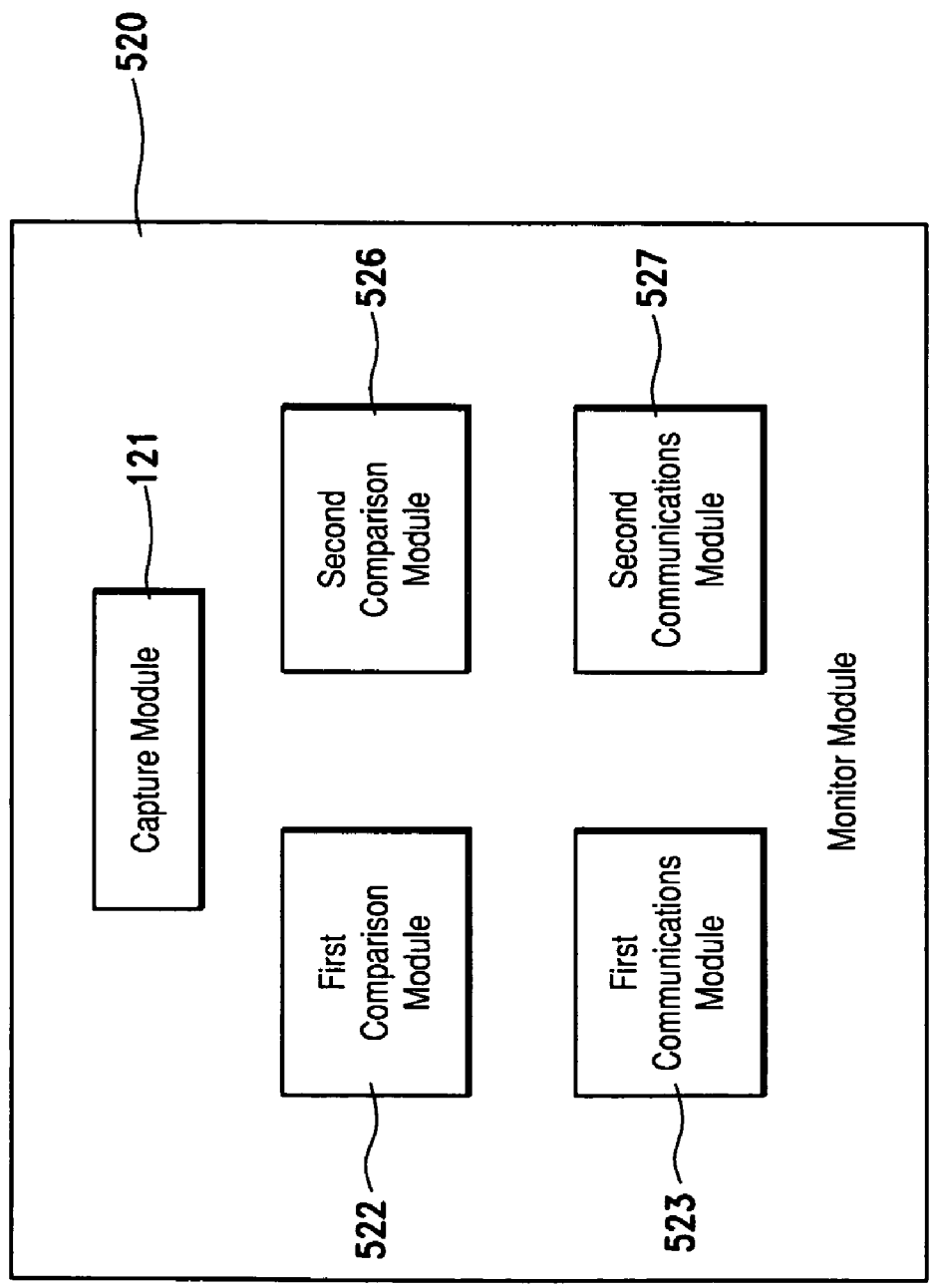
FIG. 5 illustrates a block diagram of a monitor module, according to a second embodiment.

FIG. 5 illustrates a block diagram of monitor module 520 according to a second embodiment. As an example, monitor module 520 can be used in place of monitor modules 120 and/or 125 (FIG. 1). Monitor module 520 can include capture module 121, comparison modules 522 and 526, and communications modules 523 and 527. Comparison modules 522 and 526 can be similar to comparison modules 122 (FIG. 1), and communications modules 523 and 527 can be similar to communications module 123 (FIG. 1).

Comparison module 522 can be used to check for changes in a first context, and comparison module 526 can be used to check for changes in a second context. For example, in the medical field, comparison module 522 can be used to check for changes in the patient ID, and comparison module 526 can be used to check for changes in the user login information.

In another embodiment, comparison module 522 can be used to check for context changes in a first type of event, and comparison module 526 can be used to check for context changes in a second type of event. For example, comparison module 522 can check for context changes in mouse clicks events, and comparison module 526 can be used to check for context changes in all other event types.

Communications module 523 can be used to communicate a change in a first context to application 110 (FIG. 1), and communications module 527 can be used to communicate a change in a second context to application 110 (FIG. 1). In another example, communications module 523 can communicate directly context changes for one or more first contexts from target application 192 (FIG. 1) to application 110 (FIG. 1), and communications module 527 can be used to write the data regarding the context change in one or more second contexts to a memory location and notify application 110 (FIG. 1) that data has been written to memory.

Figure 6:
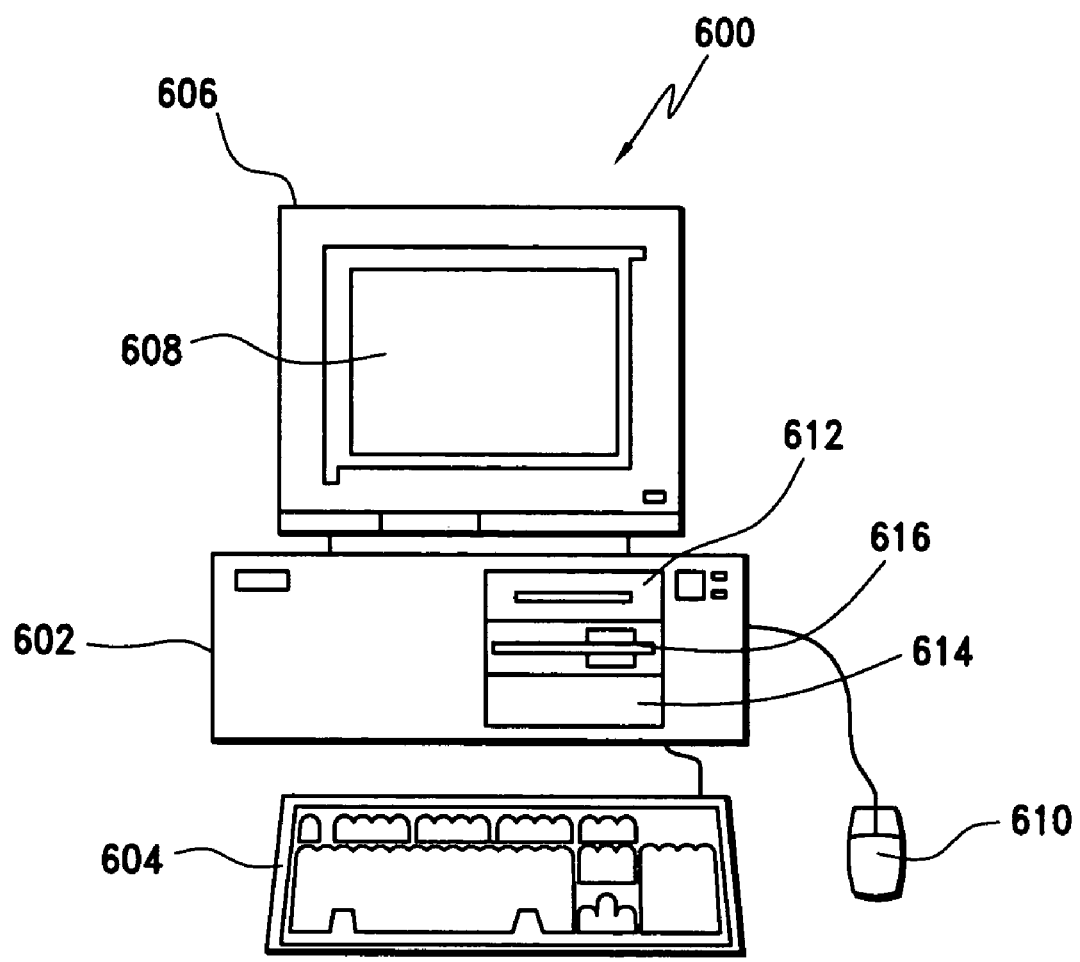
FIG. 6 illustrates a computer that is suitable for implementing an embodiment of the system of FIG. 1.
Figure 7:
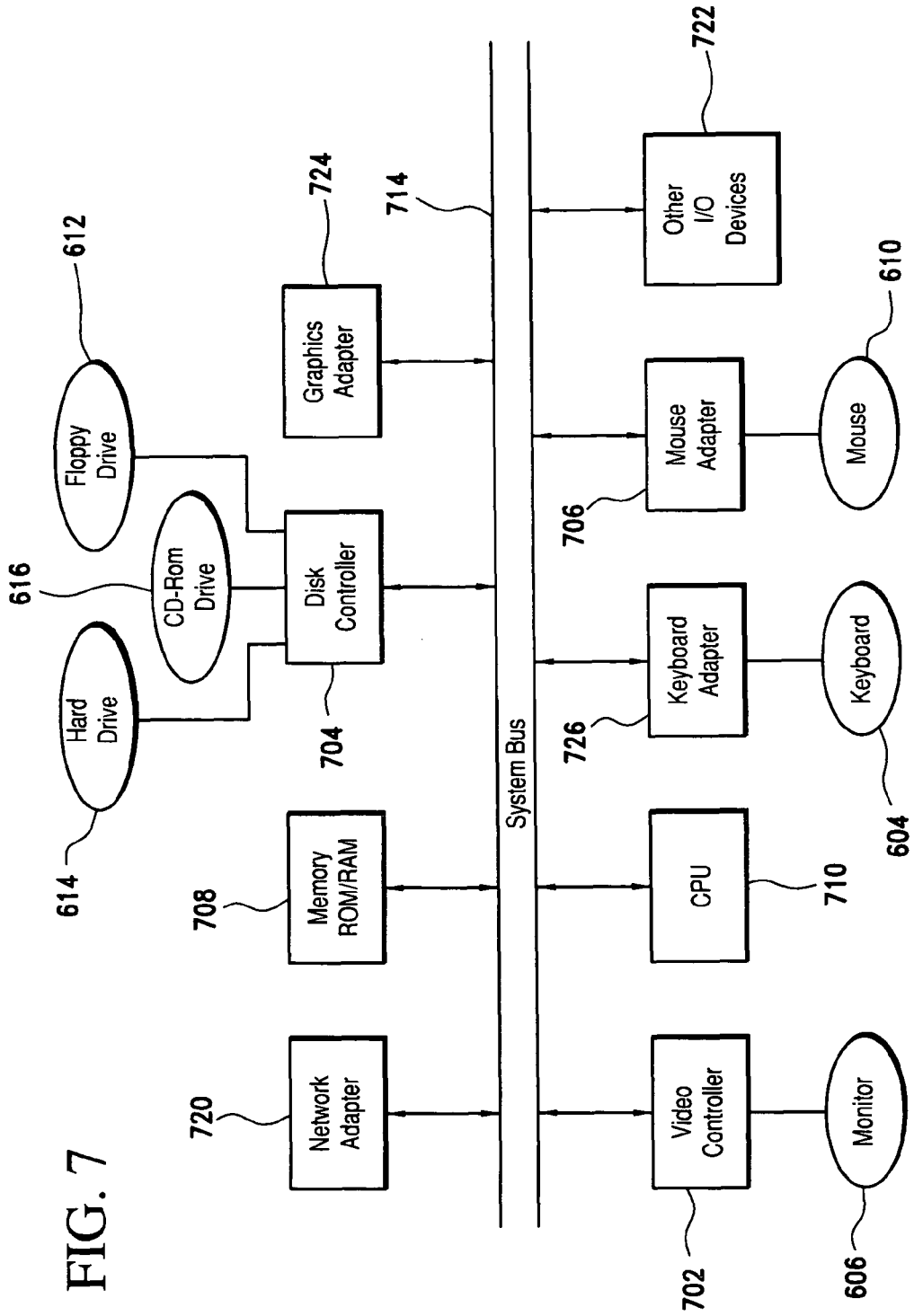
FIG. 7 illustrates a representative block diagram of the elements included on the circuit boards inside the chassis of the computer of FIG. 6.

FIG. 6 illustrates a computer 600 that is suitable for implementing an embodiment of system 100 (FIG. 1). Computer 600 includes a chassis 602 containing one or more circuit boards (not shown), a floppy drive 612, a Compact Disc Read-Only Memory (CD-ROM) drive 616, and a hard drive 614. A representative block diagram of the elements included on the circuit boards inside chassis 602 is shown in FIG. 7. A central processing unit (CPU) 710 in FIG. 7 is coupled to a system bus 714 in FIG. 7. In various embodiments, the architecture of CPU 710 can be compliant with any of a variety of commercially distributed architecture families including the RS/6000 family, the Motorola 68000 family, or the Intel x86 family.

System bus 714 also is coupled to memory 708 that includes both read only memory (ROM) and random access memory (RAM). Non-volatile portions of memory 708 (ROM) can be encoded with a boot code sequence suitable for restoring computer 600 (FIG. 6) to a functional state after a system reset. In addition, memory 708 can include microcode such as a Basic Input-Output System (BIOS).

In the depicted embodiment of FIG. 7, various I/O devices such as a disk controller 704, a graphics adapter 724, a video controller 702, a keyboard adapter 726, a mouse adapter 706, a network adapter 720, and other I/O devices 722 can be coupled to system bus 714. Keyboard adapter 726 and mouse adapter 706 are coupled to a keyboard 604 (FIGS. 6 and 7) and a mouse 610 (FIGS. 6 and 7), respectively, of computer 600 (FIG. 6). While graphics adapter 724 and video controller 702 are indicated as distinct units in FIG. 7, it will be appreciated that video controller 702 can be integrated into graphics adapter 724, or vice versa. Video controller 702 is suitable for refreshing a monitor 606 (FIGS. 6 and 7) to display images on a screen 608 (FIG. 6) of computer 600 (FIG. 6). Disk controller 704 can control hard drive 614 (FIGS. 6 and 7), floppy drive 612 (FIGS. 6 and 7), and CD-ROM drive 616 (FIGS. 6 and 7). In other embodiment, distinct units can be used to control each of these devices separately.

Although many other components of computer 600 (FIG. 6) are not shown, such components and their interconnection are well known to those of ordinary skill in the art. Accordingly, further details concerning the construction and composition of computer 600 and the circuit boards inside chassis 602 (FIG. 6) need not be discussed herein.

When the computer 600 in FIG. 6 is running, program instructions stored on a floppy disk in floppy drive 612, on a CD-ROM in CD-ROM drive 616, on hard drive 614, or in memory 708 (FIG. 7) are executed by CPU 710 (FIG. 7). A portion of the program instructions, stored on these devices, can be suitable for carrying out the method of monitoring a target application with system 100 (FIG. 1) as described previously with respect to FIGS. 1-5.

Although the invention has been described with reference to specific embodiments, it will be understood by those skilled in the art that various changes may be made without departing from the spirit or scope of the invention. Accordingly, the disclosure of embodiments of the invention is intended to be illustrative of the scope of the invention and is not intended to be limiting. It is intended that the scope of the invention shall be limited only to the extent required by the appended claims. For example, to one of ordinary skill in the art, it will be readily apparent that processes 251-257 of FIG. 2 or any element of FIG. 1 may be comprised of many different steps and be performed by many different modules, and that the foregoing discussion of certain of these embodiments does not necessarily represent a complete description of all possible embodiments. For example, in some embodiments, step 257 of FIG. 2 is not performed, and the context is not changed in foreign applications 190 (FIG. 1). In another example, system 100 (FIG. 1) and method 200 (FIG. 2) described herein are not limited to reading contexts. System 100 (FIG. 1) and method 200 (FIG. 2) can be used to monitor and detect any type of actions or behaviors of target applications 192 and 193 (FIG. 1). Additionally, monitor module 520 in FIG. 5 can have two or more capture modules similar to capture module 121, and computer 600 in FIG. 6 can be replaced with a computer network.

All elements claimed in any particular claim are essential to the invention claimed in that particular claim. Consequently, replacement of one or more claimed elements constitutes reconstruction and not repair. Additionally, benefits, other advantages, and solutions to problems have been described with regard to specific embodiments. The benefits, advantages, solutions to problems, and any element or elements that may cause any benefit, advantage, or solution to occur or become more pronounced, however, are not to be construed as critical, required, or essential features or elements of any or all of the claims.

Moreover, embodiments and limitations disclosed herein are not dedicated to the public under the doctrine of dedication if the embodiments and/or limitations: (1) are not expressly claimed in the claims; and (2) are or are potentially equivalents of express elements and/or limitations in the claims under the doctrine of equivalents.

What is claimed is:

1. A system for monitoring a target application, wherein the system, an operating system, and the target application are configured to be performed using one or more central processing units, the system comprising:
    the one or more central processing units; a processor; and a memory;
    an application extender module configured to be performed using the one or more central processing units and comprising:
        a foreign communications module to communicate a change in a first context in the target application to one or more foreign applications; and
    a first monitor module configured to be performed using the one or more central processing units and comprising:
        a capture module configured to modify one or more lookup tables in at least one of the operating system or the target application to direct first communications from at least one of the operating system or the target application and to the capture module, the capture module is further configured to receive the first communications that were directed by modifying the one or more lookup tables;
        a comparison module to test whether an event includes the change in the target application of the first context by examining the first communications to determine whether the first communications includes information regarding the change in the first context in the target application; and
        a first communications module configured to communicate the change in the first context out of the target application and to the application extender module.

2. The system of claim 1, wherein:
    the first monitor module is configured to be injected into the target application.

3. The system of claim 1, wherein:
    the application extender module is separate from the target application; and
    the application extender module further comprises:
        an injection module to inject the first monitor module into the target application.

4. The system of claim 1, wherein:
    the application extender module further comprises:
        a monitor shim module to communicate to the first monitor module the first context to be monitored.

5. The system of claim 1, wherein:
    the capture module is configured to use hooks to capture the event in the target application.

6. The system of claim 1, wherein:
    the comparison module is further capable of testing whether the event includes a change in the target application of a second context.

7. The system of claim 6, wherein:
    the first communications module is further capable of communicating the change in the second context out of the target application to the application extender module; and
    the foreign communications module is further capable of communicating the change in the second context in the target application to the one or more foreign applications.

8. The system of claim 1, wherein:
    the first monitor module further comprises:
        a second comparison module to test whether the event includes a change in the target application of a second context.

9. The system of claim 8, wherein:
    the first monitor module further comprises:
        a second communications module capable of communicating the change in the second context out of the target application to the application extender module.

10. The system of claim 1, wherein:
    the first monitor module further comprises:
        a retrieval module to obtain the first context from the target application after the comparison module has detected the change in the first context.

11. A system capable of controlling one or more foreign applications, wherein one or more target applications and an operating system are run on one or more processors of a first computer, the system comprising:
    the one or more processors of the first computer; and a memory;
    one or more first monitor modules configured to be run on the one or more processors of the first computer and further configured to detect at least one change in one or more contexts in the one or more target applications by monitoring internal communications of the one or more target applications or by monitoring communications between the one or more target applications and the operating system; and
    an extension manager application separate from the one or more target applications, configured to be run on the one or more processors of the first computer and comprising:
        a foreign communications module capable of communicating the at least one change in the one or more contexts to the one or more foreign applications, wherein:
    the one or more first monitor modules are each part of a different one of the one or more target applications; and
    the one or more first monitor modules are configured to monitor the internal communications of the one or more target applications or to monitor the communications between the one or more target applications and the operating system by accessing internal message traffic within the first computer, the operating system, and the one or more target applications.

12. The system of claim 11, wherein:
    the one or more first monitor modules are capable of communicating the at least one change in the one or more contexts from the one or more target applications to the extension manager application.

13. The system of claim 11, wherein:
    the extension manager application further comprises:
        a monitor shim module capable of instructing the one or more first monitor modules to monitor for one or more changes in the one or more contexts.

14. The system of claim 13, wherein:
    the monitor shim module is further capable of sending and receiving communications to and from the one or more first monitor modules.

15. The system of claim 11, wherein:
    the one or more first monitor modules intercept information about the one or more contexts that is communicated between the operating system and the one or more target applications.

16. The system of claim 11, wherein:
    a first one of the one or more first monitor modules is part of a first one of the one or more target applications;

a second one of the one or more first monitor modules is part of a second one of the one or more target applications;

the first one of the one or more first monitor modules intercepts information about the one or more contexts that is communicated between the operating system and the first one of the one or more target applications; and the second one of the one or more first monitor modules intercepts information about the one or more contexts that is communicated between the operating system and the second one of the one or more target applications.

17. The system of claim 11, wherein:
the one or more first monitor modules intercepts information about the one or more contexts being communicated within the one or more target applications.

18. The system of claim 11, wherein:
a first one of the one or more first monitor modules is part of a first one of the one or more target applications;
a second one of the one or more first monitor modules is part of a second one of the one or more target applications;
the first one of the one or more first monitor modules intercepts information about the one or more contexts that is communicated within the first one of the one or more target applications; and
the second one of the one or more first monitor modules intercepts information about the one or more contexts that is communicated within the second one of the one or more target applications.

19. The system of claim 11, wherein:
a first one of the one or more first monitor modules is part of a first one of the one or more target applications;
a second one of the one or more first monitor modules is part of a second one of the one or more target applications;
the first one of the one or more first monitor modules comprises:
a first capture module capable of capturing information in the first one of the one or more target applications; and
the second one of the one or more first monitor modules comprises:
a second capture module capable of capturing information in the second one of the one or more target applications.

20. The system of claim 19, wherein:
the first one of the one or more first monitor modules further comprises:
a first comparison module capable of testing and determining whether the one or more contexts in the first one of the one or more target applications have changed by using the information captured by the first capture module; and
a first communications module capable of communicating a change in the one or more contexts in the first one of the one or more target applications to the extension manager application; and
the second one of the one or more first monitor modules further comprises:
a second comparison module capable of testing and determining whether the one or more contexts in the second one of the one or more target applications have changed by using the information captured by the second capture module; and
a second communications module capable of communicating a change in the one or more contexts in the second one of the one or more target applications to the extension manager application.

21. A method to monitor one or more target applications, the method comprising:

executing one or more first computer instructions configured to wait for communications that a potential first event has occurred in a first target application of the one or more target applications;

executing one or more second computer instructions configured to capture the communications containing the potential first event in the first target application of the one or more target applications, executing the one or more second computer instructions configured to capture the communications comprises:
receiving the communications that the potential first event has potentially occurred in the first target application of the one or more target applications;

executing one or more third computer instructions configured to test in the first target application of the one or more target applications whether the potential first event includes a change in a first context;

if the potential first event includes the change in the first context, executing one or more fourth computer instructions configured to transmit first data indicating the change in the first context from the first target application of the one or more target applications to an extension manager application; and afterwards, executing one or more fifth computer instructions configured to transmit the change in the first context from the extension manager application to one or more foreign applications, wherein:
the communications are internal communications of the first computer.

22. The method of claim 21, wherein:
executing the one or more fourth computer instructions configured to transmit the first data from the first target application to the extension manager application further comprises:
executing the one or more fourth computer instructions configured to transmit the first data from the first target application to the extension manager application only if the potential first event includes the change in the first context.

23. The method of claim 21, further comprising:
executing one or more sixth computer instructions configured to communicate the first context from the extension manager application to the first target application.

24. The method of claim 21, wherein:
executing the one or more second computer instructions configured to capture the communications containing the potential first event further comprises:
executing one or more sixth computer instructions configured to use a monitor module in the first target application of the one or more target applications to capture the potential first event in the first target application;

executing the one or more third computer instructions configured to test in the first target application of the one or more target applications further comprises:
executing one or more seventh computer instructions configured to use the monitor module to test whether the potential first event includes the change in the first context; and executing the one or more fourth computer instructions configured to transmit the first data from the first target application of the one or more target applications to the extension manager application further comprises:
executing one or more eighth computer instructions configured to use the monitor module to transmit the first data indicating the change from the first target application of the one or more target applications to the extension manager application.

25. The method of claim 21, further comprising:
before executing the one or more second computer instructions configured to capture the potential first event in the first target application of the one or more target applications, executing one or more sixth computer instructions configured to inject the monitor module into the first target application of the one or more target applications.

26. The method of claim 21, further comprising:
after executing the one or more fourth computer instructions configured to transmit the change in the first context from the extension manager application to the one or more foreign applications, executing one or more sixth computer instructions configured to change the first context in the one or more foreign applications.

27. The method of claim 21, wherein:
executing the one or more second computer instructions configured to capture the communications containing the potential first event comprises:
    executing one or more sixth computer instructions configured to intercept the potential first event while the potential first event is being communicated between the first target application of the one or more target applications and an operating system.

28. The method of claim 21, wherein:
executing the one or more second computer instructions configured to capture the communications containing the potential first event comprises:
    executing one or more sixth computer instructions configured to intercept the potential first event while the potential first event is being communicated within the first target application of the one or more target applications.

29. The method of claim 21, further comprising:
executing one or more sixth computer instructions configured to test in the first target application of the one or more target applications whether the potential first event includes a change in a second context;
if the potential first event includes the change in the second context, executing one or more seventh computer instructions configured to transmit second data indicating the change in the second context from the first target application of the one or more target applications to the extension manager application; and
afterwards, executing one or more eighth computer instructions configured to transmit the change in the second context from the extension manager application to the one or more foreign applications.

30. The method of claim 29, wherein:
executing the one or more sixth computer instructions configured to test whether the potential first event includes the change in the second context further comprises:
    executing one or more ninth computer instructions configured to use a monitor module to test whether the potential first event includes the change in the second context; and
executing the one or more seventh computer instructions configured to transmit the second data from the first target application to the extension manager application further comprises:
    executing one or more tenth computer instructions configured to use the monitor module to transmit the second data indicating the change in the second context from the first target application to the extension manager application.

31. The method of claim 21, further comprising:
executing one or more sixth computer instructions configured to capture communications containing a second event in a second target application of the one or more target applications;
executing one or more seventh computer instructions configured to test in the second target application whether the second event includes the change in the first context; and
if the second event includes the change in the first context, executing one or more eighth computer instructions configured to transmit third data indicating the change in the first context from the second target application to the extension manager application.

32. The method of claim 31, further comprising:
executing one or more ninth computer instructions configured to test in the second target application whether the second event includes a change in a second context;
if the second event includes the change in the second context, executing one or more tenth computer instructions configured to transmit fourth data indicating the change in the second context from the second target application to the extension manager application; and
afterwards, executing one or more eleventh computer instructions configured to transmit the change in the second context from the extension manager application to the one or more foreign applications.

33. A computer-implemented system for monitoring a target application, wherein the system is configured to be performed using one or more central processing units, the system comprising:
the one or more central processing units; a processor; and a memory;
an extension manager module configured to be performed using the one or more central processing units and comprising:
    a foreign communications module configured to run configured to communicate a change in a state of the target application to one or more foreign applications; and
at least one monitor module configured to be performed using the one or more central processing units and configured to interact with the target application, the at least one monitor module comprising:
    an interception module configured to intercept one or more event-related function calls within the target application by redirecting the one or more event-related function calls to the interception module from one or more predetermined destinations, the interception module further configured to redirect the one or more one or more event-related function calls to the one or more predetermined designations after a determination of whether the one or more event-related function calls for an event;
    a comparison module configured to determine whether the event includes the change in the state of the target application; and
a first communications module configured to communicate the change in the state out of the target application and to the extension manager module.

34. The system of claim 33, wherein:
the extension manager module is separate from the target application; and
the extension manager module further comprises:
    an injection module to inject the at least one monitor module into the target application.

35. The system of claim 33, wherein:
the interception module is configured to use hooks to intercept the one or more event-related function calls within the target application.

36. The system of claim 33, wherein:
the at least one monitor module is part of the target application.

* * * * *